US007078171B2

(12) United States Patent
Giordano et al.

(10) Patent No.: US 7,078,171 B2
(45) Date of Patent: *Jul. 18, 2006

(54) METHODS FOR IDENTIFYING NOVEL NUCLEIC ACID REGULATORY ELEMENTS AND COMPOUNDS THAT AFFECT THE REGULATION

(75) Inventors: Anthony Giordano, Phoenixville, PA (US); Paul S. Eder, Oreland, PA (US); Deborah Beach McGill, Wilmington, DE (US); Gregg Johannes, Exton, PA (US)

(73) Assignee: Message Pharmaceutical, Inc., Malvern, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 500 days.

(21) Appl. No.: 10/258,930

(22) PCT Filed: Apr. 30, 2001

(86) PCT No.: PCT/US01/13864

§ 371 (c)(1),
(2), (4) Date: Jun. 25, 2003

(87) PCT Pub. No.: WO01/84155

PCT Pub. Date: Nov. 8, 2001

(65) Prior Publication Data

US 2004/0091866 A1    May 13, 2004

Related U.S. Application Data

(63) Continuation-in-part of application No. 09/560,174, filed on Apr. 28, 2000.

(51) Int. Cl.
C12Q 1/68     (2006.01)
C12N 15/63    (2006.01)
C12N 15/64    (2006.01)

(52) U.S. Cl. .............................. 435/6; 435/7.1; 435/29; 435/455

(58) Field of Classification Search ..................... None
See application file for complete search history.

(56) References Cited

U.S. PATENT DOCUMENTS 5,641,675 A * 6/1997 Singer et al. ............... 435/325
5,773,246 A   6/1998 Keene et al. ............... 435/69.1
5,859,227 A   1/1999 Giordano et al. ........... 536/24.1
5,968,738 A  10/1999 Anderson et al. ............. 435/6
5,985,575 A * 11/1999 Wickens et al. ............... 435/6
6,083,727 A   7/2000 Guegler et al. ............. 435/91.5

FOREIGN PATENT DOCUMENTS

WO   WO 94/23041   10/1994
WO   WO 98/04923    2/1998
WO   WO 98/42854   10/1998
WO   WO 98/55502   12/1998

OTHER PUBLICATIONS

Brewer, "An A + U-Rich Element RNA-Binding Factor Regulates c-myc mRNA Stability In Vitro," Mol. Cell. Biol. 11:2460-2466 (1991).
Carrier et al., "Library of Synthetic 5' Secondary Structures To Manipulate mRNA Stability in *Escherichia Coli*," Biotechnol. Prog. 15:58-64 (1999).
Claffey, et al., "Identification of a Human VPF/VEGF 3' Untranslated Region Mediating Hypoxia-induced mRNA Stability," Molecular Biology of the Cell 9:469-481 (1998).
Donis-Keller et al., "Site Specific Enzymatic Cleavage of RNA," Nucl. Acids Res. 7:179-192 (1979).
Gao et al., "Selection of a Subset of mRNAs from Combinatorial 3' Untranslated Region Libraries Using Neuronal RNA-binding Protein He1-N1," PNAS USA 91:11207-11211 (1994).
Goldspink et al., "Localization of Cardiac α-myosin Heavy Chain mRNA is Regulated by its 3' Untranslated Region Via Mechanical Activity And Translational Block," Journal of Cell Science 110:2969-2978 (1997).
Grignani et al., "High-Efficiency Gene Transfer and Selection of Human Hematopoietic Progenitor Cells with a Hybrid EBV/Retroviral Vector Expressing the Green Fluorescence Protein," Cancer Res. 58:14-19 (1998).
Ho, et al., "Use of a Marked Erythropoietin Gene for Investigation of Its Cis-acting Elements," J. Biol. Chem. 270:10084-10090 (1995).
Izquierdo et al., "Control of the Translational Efficiency of β-F1-ATPase mRNA Depends on the Regulation of a Protein That Binds the 3' Untranslated Region of the mRNA," Molecular And Cellular Biology 17(9):5255-5268 (1997).
Kozak et al., "An Analysis of 5'-Noncoding Sequences from 699 Vertebrate Messenger RNAs," Nucl. Acids Res. 15:8125-8148 (1987).
Menotti et al., "Translational Regulation of mRNAs With Distinct IRE Sequences by Iron Regulatory Proteins 1 and 2," J. Biol. Chem. 273(3):1821-1824 (1998).
Müllner et al., "A Specific mRNA Binding Factor Regulates the Iron-Dependent Stability of Cytoplasmic Transferrin Receptor mRNA," Cell 58:373-382 (1989).

(Continued)

*Primary Examiner*—David Guzo
(74) *Attorney, Agent, or Firm*—Clark & Elbing LLP; Kristina Bieker-Brady (57) ABSTRACT

Described herein are methods for identifying novel nucleic acid regulatory elements and compounds that modulate the regulation of such elements. Also described herein are nucleic acid sequence identified as novel nucleic acid regulatory elements and host cells containing such nucleic acid regulatory elements in a vector.

5 Claims, 2 Drawing Sheets

OTHER PUBLICATIONS

Nakanishi et al., "Reduction of Syndecan-1 mRNA in Cervical-carcinoma Cells is Involved With the 3' Untranslated Region," Int. J. Cancer 80(4):527-532 (1999).

Ohlmann et al., "The Properties of Chimeric Picornavirus IRESes Show That Discrimination Between Internal Translation Initiation Sites Is Influenced by the Identity of the IRES and Not Just the Context of the AUG Codon," RNA 5:764-778 (1999).

Romeo et al., "An Element of the Transforming Growth Factor-beta 1 5'-untranslated Region Represses Translation and Specifically Binds a Cytosolic Factor," Mol. Endocrinol. 7(6):759-766 (1993).

Sharp et al., "Regulation of Chicken α and β Actin Genes And Their Hybrids Inserted Into Myogenic Mouse Cells," Gene 80:293-304 (1989).

Shaw et al., "A Conserved AU Sequence from the 3' Untranslated Region of GM-CSF mRNA Mediates Selective mRNA Degradation," Cell 46:659-666 (1986).

Spicher et al., "Highly Conserved RNA Sequences That Are Sensors of Environmental Stress," Molecular and Cellular Biology, 18:7371-7382 (1998).

Suzuki et al., "Construction And Characterization Of A Full Length-enriched And A 5'-end-enriched cDNA Library," Gene 200:149-156 (1997).

Yang et al., "The 3'-Untranslated Region of the $\alpha_{2c}$-Adrenergic Receptor mRNA Impedes Translation of the Receptor Message," J. Biol. Chem. 272:15466-15473 (1997).

Wilson et al., "An Episomal Expression Vector System For Monitoring Sequence-specific Effects on mRNA Stability in Human Cell Lines," Plasmid 33(3):198-207 (1995).

Zaidi et al., "Amyloid Precursor Protein mRNA Stability Is Controlled by a 29-Base Element in the 3'-Untranslated Region," J. Biol. Chem. 269:24007-24013 (1994).

* cited by examiner

METHODS FOR IDENTIFYING NOVEL NUCLEIC ACID REGULATORY ELEMENTS AND COMPOUNDS THAT AFFECT THE REGULATION

This application is the U.S. National Stage of International Application No. PCT/US01/13864, filed Apr. 30, 2001, which was published in English under PCT Article 21(2), and which is a continuation-in-part of U.S. Ser. No. 09/560,174, filed Apr. 28, 2000.

BACKGROUND OF THE INVENTION

While transcriptional controls can regulate expression of a gene, post-transcriptional mechanisms can also affect the ultimate level of gene expression by modulating the functional properties of the mRNA. These functional properties include the pre-mRNA processing, mRNA stability, mRNA translational efficiency, mRNA localization, mRNA sequestration, or mRNA editing and splicing (Izquierdo and Cueza, Mol. Cell Biol. 17: 5255–5268; Yang et al., J. Biol. Chem. 272: 15466–73, 1997; Ross, Microbiol. Rev. 59: 423–50, 1995). Post-transcriptional control mechanisms appear to play an especially important role in the gene expression response to environmental factors such as heat shock (Sierra et al., Mol. Biol. Rep. 19: 211–20, 1994), iron availability (Hentze et al., Proc. Natl. Acad. Sci. USA 93: 8175–82 (1996), oxygen (Levy et al., J. Biol. Chem. 271: 2746–53, 1996; McGary et al., J. Biol. Chem. 272: 8628–34, 1997), and growth factors (Amara et al., Nucleic Acids Res. 21: 4803–09, 1993).

The cis-elements that exert post-transcriptional regulatory effects on levels of protein ultimately present in a cell may be present in the 5' and/or 3' untranslated regions (UTRs) of the mRNA. At the 5' UTR, mRNA binding to ribosomes is generally the rate-limiting step in the initiation of translation (Mathews et al., In: Translational Control, pages 1–30, Eds: Hershey et al., Cold Spring Harbor Laboratory Press, Cold Spring Harbor, N.Y., 1996). At the 3' UTR, regulatory elements may modulate mRNA translation and degradation, as well as mRNA transport and subcellular localization (Jackson, Cell 74: 9–14, 1993).

SUMMARY OF THE INVENTION

In general, the invention features a novel method for screening nucleic acid sequences, derived from the mRNA untranslated regions (UTRs) of genes of therapeutic interest, to identify UTRs that contain novel post-transcriptional regulatory elements. Sequences identified in the UTR screen as containing such regulatory elements are then used as targets in secondary screens to identify therapeutic agents that affect the UTR regulatory function and, ultimately, affect gene expression. The UTR elements found using the methods of the invention may also be used to regulate expression of a protein from a heterologous sequence.

Accordingly, in a first aspect, the invention features a method of identifying a nucleic acid sequence, derived from the mRNA untranslated region (UTR) of a gene, that has a physiologically relevant post-transcriptional regulatory function. The method involves identifying a 5' or 3' UTR sequence from a gene of interest; selecting host cells which express the gene that is endogenously associated with the UTR; transfecting one set of host cells with a test expression vector, where the test vector includes the 5' or 3' UTR sequence linked to, and positioned upstream or downstream, respectively, of a reporter gene construct (UTR/reporter), and transfecting another set of host cells with a control expression vector, where the control vector contains the reporter gene and lacks the UTR sequence (control/reporter). The method further involves identifying whether the UTR sequence has a post-transcriptional regulatory function by assessing whether a first mRNA function of the UTR/reporter transcript is changed compared to the control/reporter transcript; and determining whether the UTR regulatory function identified above is physiologically relevant by assessing whether the changed first mRNA function of the UTR/reporter transcript corresponds to the first mRNA function of the gene endogenously associated with the UTR.

In one embodiment of the invention, the method additionally involves confirming the physiological relevance of the UTR regulatory function by assessing whether a second mRNA function of the UTR/reporter transcript corresponds to the second mRNA function of the UTR-associated endogenous gene. In another embodiment, the mRNA function is selected from the group consisting of pre-mRNA processing, mRNA stability, mRNA translational efficiency, mRNA localization, mRNA sequestration, and mRNA editing and splicing. In yet another embodiment, the UTR/reporter further contains a second UTR sequence from the gene of interest, where the UTR/reporter includes both the 5' UTR and the 3' UTR sequences of the gene, positioned upstream and downstream, respectively, of the reporter gene. In still another embodiment, the UTR sequence is the full length untranslated sequence derived from the mRNA untranslated region of a gene. In yet another embodiment, a nucleic acid corresponding to the UTR/reporter and/or to the control/reporter is stably integrated into a chromosome of the host cell(s).

In a second aspect, the invention features a population of host cells containing at least one cell transfected with a test expression vector which contains a UTR sequence linked to a reporter gene construct (UTR/reporter). The population of host cells further includes at least one other host cell transfected with a control expression vector, which includes the reporter gene and lacks UTR sequence (control/reporter), and where the host cells endogenously express the gene associated with the UTR. In one embodiment, a nucleic acid corresponding to the UTR/reporter and/or to the control/reporter is stably integrated into a chromosome of the host cell(s).

In a third aspect, the invention features a nucleic acid sequence identified as having a physiologically relevant post-transcriptional regulatory function by the method of the first aspect of the invention.

In a fourth aspect, the invention features a method of identifying candidate compounds having an effect on expression of a gene of interest. The method involves identifying UTR sequences having post-transcriptional regulatory function by the method of the first aspect of the invention; contacting the compound with an mRNA molecule containing the UTR sequence; and measuring whether the compound alters a UTR-mediated effect.

In one embodiment of the fourth aspect of the invention, the compound is contacted with a cell that expresses the mRNA molecule. In one embodiment, the measured UTR-mediated effect is the expression of a gene linked to the UTR sequence. In another embodiment, the UTR-mediated effect is a change in mRNA function. In yet another embodiment, the compound is contacted with the RNA molecule in vitro, and the UTR-mediated effect is an interaction between an mRNA transcript containing the UTR and an RNA binding protein.

By a "post-transcriptional regulatory function" is meant an effect mediated by a nucleic acid sequence found in the untranslated region (UTR) of the gene's mRNA transcript that modulates the function of the mRNA or pre-mRNA and can ultimately affect the level of expression of the gene. Examples of mRNA or pre-mRNA functions that can be modulated include pre-mRNA processing, mRNA stability, mRNA translational efficiency, mRNA localization, mRNA sequestration, or mRNA editing and splicing. The mRNA function can be assessed, for example, by measuring the half-life of the transcript (Saulnier-Blache et al., Mol. Pharmacol. 50: 1432–1442, 1996; Yang et al., J. Biol. Chem. 272: 15466–15473, 1997), polysomal distribution along the transcript (Izquierdo et al., Mol. Cell Biol. 17: 5255–5268, 1997; Luis et al., J. Biol. Chem. 268: 1868–1875, 1993; Santaren et al., J. Biochem. 113: 129–131, 1993), the type of polysome associated with the transcript, or the transcript's intracellular distribution (Yang et al., 1997, supra). Any of the above measures of function for a UTR-associated transcript that differs by 20% or more above or below the value for the corresponding UTR-free transcript indicates that the UTR alters mRNA function. An increase in the half-life (or a decrease in degradation rate) of the full length transcript indicates an increase in mRNA stability; an increase in transcript length, or an increase in the transcript's association with high molecular weight polysomes, indicates an increase in translational efficiency; and an increase in a transcript's relative distribution in the cytosol indicates in increase in transport out of the nucleus.

By a "physiologically relevant" post-transcriptional regulatory function is meant a function associated with a UTR that occurs in vivo during expression of a gene in a cell's genome and which can affect the level of protein expressed.

By a "gene of interest" is meant a gene implicated in the cause or prevention of a disease or condition such that modulating the level of its expression could be therapeutically beneficial. By a "gene that is endogenously associated with the UTR" is meant the gene from which the UTR is identified, wherein the mRNA transcribed from the gene in a cell's genome contains the UTR sequence.

By a "UTR sequence" is meant a nucleic acid sequence derived from the 5' or 3' UTR of a gene, wherein said sequence is composed of nine or more contiguous nucleotides, said nucleotides being outside of the coding region of a gene of interest. More desirably, the UTR is the full length UTR sequence of a gene of interest.

By a "changed" mRNA function is meant that the value of an mRNA function in a UTR/reporter transcript is altered such that the corresponding value for the control/reporter transcript varies by at least 20% from the UTR/reporter value.

By "corresponds to the mRNA function of a gene endogenously associated with the UTR" is meant a value of an mRNA function in a reporter transcript that is equivalent to the corresponding value for the transcript of the endogenous gene such that the endogenous transcript's value varies by less than 20% from the reporter transcript value.

By "confirming the physiological relevance of said UTR regulatory function" is meant determining that more than one mRNA function in a UTR/reporter transcript are equivalent to the corresponding values for the transcript of the endogenous UTR associated gene.

By a "UTR-mediated effect" is meant a post-transcriptional change that can ultimately result in altered expression of the UTR associated gene. Such an effect can be detected as a change in gene expression, mRNA function, or RNA/RBP binding pair interaction.

By an "RNA/RBP binding pair interaction" is meant a physical association between an RNA molecule and an RBP, or an RBP complex made up of more than one protein, that is based on the specific characteristics of the interacting molecules, and is not inhibited by nonspecific competitor molecules present at a concentration equivalent to the interacting molecules. The RNA and RBP molecules that form the RNA/RBP binding pair interaction can be separated from their counterpart, non-associated molecules by filter binding assay, electrophoretic mobility assay, homopolymer beads, or fluorescent anisotrophy assay.

A nucleic acid molecule or nucleic acid segment referred to as having a specific nucleic acid sequence is intended to mean a nucleic acid molecule in any of its corresponding forms, for example, DNA, cDNA, RNA, or mRNA.

Other features and advantages of the invention will be apparent from the following detailed description and from the claims.

BRIEF DESCRIPTION OF THE DRAWINGS

FIGS. 1A and 1B are pictures of northern blots showing the polysome analysis of endogenous, UTR/reporter, and control/reporter mRNAs. "Her2" denotes the endogenous Her2 mRNA in MCF-7 cells. "Luc-Her2-3' UTR" denotes a chimeric mRNA containing the 5' UTR from a luciferase reporter, the luciferase reporter coding sequence, and the 3' UTR of Her2. "Luc" denotes a luciferase mRNA containing the 5' UTR, coding sequence, and 3' UTR from a luciferase reporter construct. MCF-7 cells were stably transfected with the Luc-Her2-3' UTR or the Luc construct using standard methods. Cells containing the endogenous Her2 nucleic acid, the Luc-Her2-3' UTR chimeric nucleic acid, or the luciferase nucleic acid were analyzed using standard polysome analysis (see, for example, Johannes and Sarnow, RNA 4:1500–1513, 1998). The lanes of the northern blots are numbered based on the number of ribosomes associated with each mRNA molecule. As illustrated in FIGS. 1A and 1B, endogenous Her2 mRNA and the chimeric Luc-Her2-3' UTR mRNA are predominantly associated with high molecular weight (HMW) polysomes.

FIGS. 2A and 2B demonstrate that a smaller percentage of the chimeric Luc-Her2-3' UTR mRNA and the luciferase mRNA are associated with HMW polysomes in transiently transfected cells than in stably transfected cells.

DETAILED DESCRIPTION

We have discovered a novel method for screening nucleic acid sequences, derived from the mRNA untranslated regions (UTRs) of genes of therapeutic interest, to identify UTRs that contain novel post-transcriptional regulatory elements that have physiologically relevant functions. Sequences identified in the UTR screen as containing such regulatory elements are then used as targets in secondary screens to identify compounds that affect the UTR regulatory function and, ultimately, affect gene expression. These sequence may also be used to modulate expression of a protein encoded by a heterologous nucleic acid sequence.

The UTR screening method of the present invention is advantageous because it selects for UTR sequences with post-transcriptional regulatory elements that are physiologically relevant. This selection is achieved through a two step process. First UTR sequences are linked to reporter genes and those sequences that post-transcriptionally regulate an mRNA function in the reporter gene transcript are selected. Next, the corresponding mRNA function of the endogenous genes associated with the identified UTR sequences is measured to determine the physiological relevance of the regulatory effect. Those UTR sequences that alter an mRNA function in the reporter transcript in a manner that corresponds to the mRNA function of the endogenous transcript are considered to be physiologically relevant.

The physiologically relevant function of the identified UTR sequences makes them ideal candidates for secondary compound screens because compounds which modulate the function of these sequences in reporter screening assays will also modulate the endogenous UTR function. Accordingly, compounds identified by these secondary screens as regulating UTR function are promising candidate drugs for use in modulating the expression of the therapeutically relevant genes that are endogenously associated with the UTRs.

1. UTR Sequences, Reporter Constructs, and Host Cells

The first step of the assay includes choosing the UTR sequences to screen. Any known 5' or 3' UTR mRNA sequence derived from a gene of interest may be used. Data bases such as GenBank, EMBL, and DDBJ may be searched to obtain the sequence information for desired UTRs. In addition, a UTR database can be found at the internet site bigarea.area.cnr.it:8000/biowww/#utrdb. Ideally, the UTR is from a gene that encodes a therapeutically relevant protein, such as a protein implicated in the causation or prevention of a disease. Additionally, other sequences that can be used include any UTR sequence found in the cDNA library of full length 5' and 3' UTR sequences created by the method described in provisional application U.S. Ser. No. 60/142,217. The UTR sequences used for screening include those in which there is no prior information regarding their post-transcriptional regulatory function.

To construct the test vectors used for transfecting host cells, a purified double-stranded cDNA that corresponds to a 5' or 3' UTR sequence is synthesized and ligated into an expression vector of choice. The 5' or 3' sequence, uncoupled from its normal association with the adjoining sequences of the gene, is instead positioned upstream or downstream, respectively, of a reporter gene's coding sequence (UTR/reporter). It is desirable that the UTR/reporter constructs contain both the 5' and 3' UTR sequences. It is also desirable that the UTR sequence be full length, although UTR sequences which are less than full length (for example, a sequence containing nine or more contiguous nucleotides) may also be used.

The vectors used as controls contain the reporter gene sequence free from association with any UTR sequence (control/reporter). Promoters which may be used include constitutive promoters, for example, CMV, RSV, or SV40; inducible promoters, such as the Tet-inducible promoter; or the endogenous promoter from the gene of interest. Examples of reporter genes that could be used include sequences encoding chloramphenicol acetyltransferase, firefly luciferase, renilla luciferase, β-galactosidase, secreted alkaline phosphatase, human growth hormone, β-glucuronidase, green fluorescent peptide, red fluorescent protein, or any polypeptide for which levels can be quantitated by standard assays (ELISA, fluorescence intensity, etc.) (Ausubel et al., Current Protocols in Molecular Biology, John Wiley & Sons, 1995).

DNA encoding UTR sequences can be obtained from available clones, by synthesizing a DNA molecule with a known nucleic acid sequence, or by cloning the gene encoding the UTR sequence. Purified 5' and 3' UTR RNA fragments can be subjected to 5' RACE (Rapid Amplification of cDNA Ends) to obtain double-stranded cDNA (Frohman, In: PCR Protocols: A Guide to Methods and Applications, pages 28–38, Eds: Innis et al., Academic Press, London). Methods for cloning genes encoding known RNA molecules and proteins of interest and techniques for recombinant expression are well described in the literature (Sambrook et al., Molecular Cloning, Cold Spring Harbor Laboratory, 1989). Commercial kits are also available (mCap RNA capping kit, Stratagene, La Jolla, Calif.). Transfection of host cells with the test vectors or control vectors is performed using standard transfection techniques (Ausubel et al., Current Protocols in Molecular Biology, John Wiley & Sons, 1995). In one desirable embodiment, retroviral vectors are used for transfection. Examples of standard stable transfection methods include calcium phosphate transfection, electroporation, and liposome-mediated transfection (Ausubel et al., supra).

The host cells used for transfection of the UTR/reporter or control/reporter construct also endogenously express the UTR sequence in association with its naturally linked gene. These cells are used for the purpose of assessing the physiological relevance of any identified UTR-associated post-transcriptional regulatory effect, as further discussed below. The test cells selected for screening express the reporter gene at levels equivalent to or less than the expression of the endogenous UTR-associated gene in the host cells. Reporter gene levels may be quantified, for example, by quantitative rtPCR, Northern analysis, or ribonuclease protection assay (RPA). Ideally, when the expression levels of a reporter gene and an endogenous UTR-associated gene are less than 2 fold different, the levels are considered to be equivalent. However, if higher expression levels are obtained, the endogenous gene properties (stability, abundance level, and polysomes distribution) can be analyzed in the transfected cell, for example, by titrating out a binding protein to ensure that the increased expression did not alter any of these properties.

By mimicking the level of expression of the endogenous gene, one increases the likelihood that a UTR sequence that post-transcriptionally regulates gene expression will be identified in the UTR/reporter screen. If the expression level of the UTR/reporter transcript is substantially different from the endogenous UTR-associated gene, this change may alter the normal function of the UTR sequence such that no regulatory effect is detected. For example, an equivalent level of expression may be critical to detect the regulatory function of a UTR that destabilizes the mRNA transcript through interaction with an RNA binding protein (RBP). If the expression of the UTR/reporter significantly exceeds expression of the endogenous UTR-associated gene, the RBP concentration may be a limiting factor in the RBP interaction with the UTR/reporter transcript. Thus, the destabilizing effect of the interaction may not be detected because the population of UTR/reporter transcripts as a whole is not subject to a significant number of RNA/RBP destabilizing interactions.

If the UTR/reporter is expressed at high levels, however, the existence of a RBP that destabilizes the mRNA could be detected as an increased expression of the endogenous gene. This increase in expression of the endogenous gene would indicate that the presence of excess UTR/reporter transcript reduces the RBP interaction with the endogenous transcript, resulting in increased stability of the endogenous transcript and increased endogenous gene expression.

Cells that are stably transfected with a UTR/reporter construct may better mimic the conditions of the endogenous mRNA than cells that are transiently transfected with a UTR/reporter construct. For example, the polysome distribution of a UTR/reporter transcript containing the firefly luciferase reporter mRNA operably linked to the 3' UTR of Her2 was determined for both cells stably transfected with the reporter construct and cells transiently transfected with the reporter construct (U.S. Provisional Application No. 60/278,902, filed Mar. 26, 2001).

To generate cells in which the reporter sequence is stably integrated into a chromosome of the cells, 1 million MCF-7 cells in a well of a six-well pate were transfected with 2 μg supercoiled plasmid (pCI-neo or pRcRSV) using Lipofectin (Life Technologies) or Fugene (Roche). One plasmid was a "Luc-Her2-3' UTR" construct encoding a chimeric mRNA containing the 5' UTR from a luciferase reporter, the luciferase reporter coding sequence, and the 3' UTR of Her2. The other plasmid contained the 5' UTR, coding sequence, and 3' UTR of firefly luciferase. The transfected cells were maintained in media containing the G418 selecting antibiotic at 500 μg/ml. The cells were analyzed 12–14 weeks later to determine the polysome profiles for endogenous Her2, heterologous Luc-Her2-3' UTR, or heterologous luciferase mRNA.

For the transient transfections, 0.01 μg of plasmid was transfected using Fugene into 0.25 million cells in a well of a 24-well plate. The "Luc" and "Luc-Her2-3' UTR" constructs used to transfect the cells each contained a 5' UTR of luciferase, a luciferase coding sequence, and either a 3' UTR of luciferase or a 3' UTR of Her2, respectively. The Luc-Her2-3' UTR construct was generated from the firefly luciferase pGL3-Control plasmid using standard molecular biology techniques. Polysome distribution analysis of the Luc-Her2-3' UTR and the luciferase mRNA transcripts was conducted 48 hours after the transient transfection.

Figures 1A, 1B:
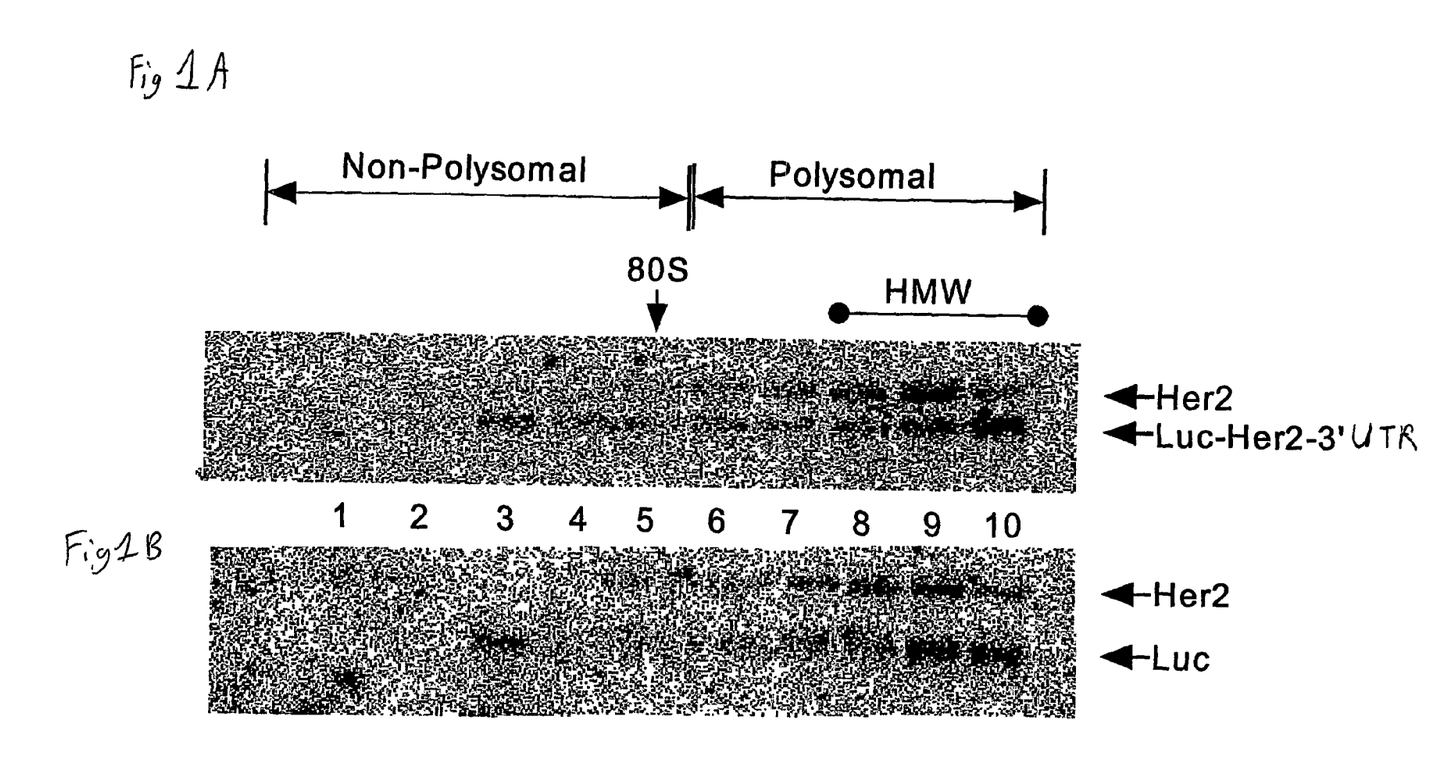
Figure 2A:
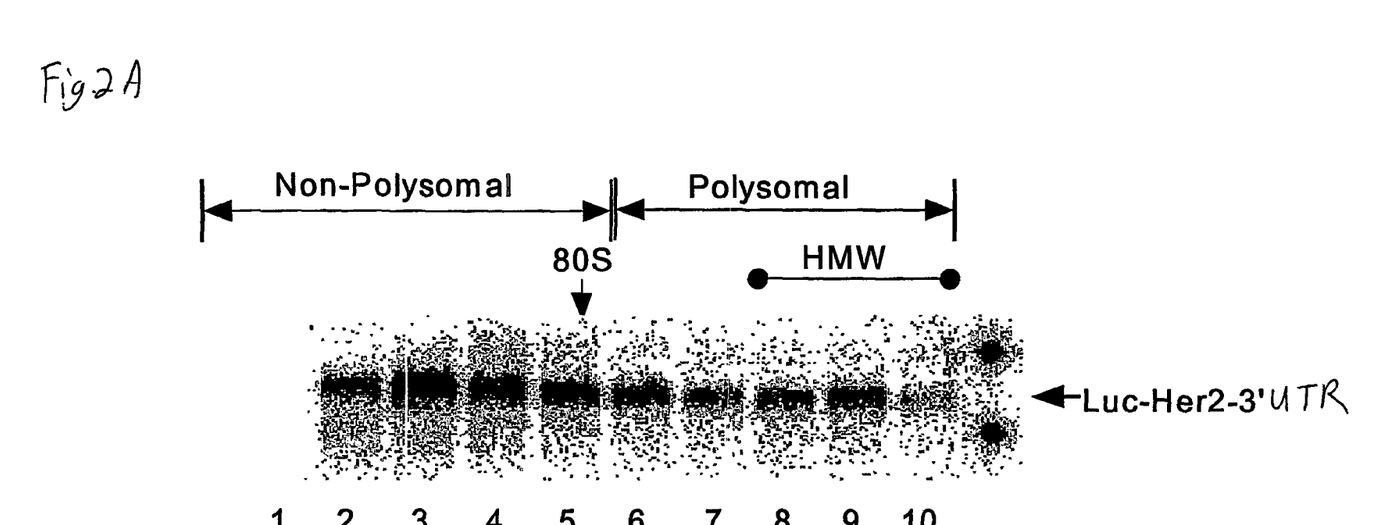
FIGS. 2A and 2B are pictures of northern blots showing the polysome analysis of UTR/reporter and control/reporter mRNAs in transiently transfected cells. As described above, "Luc-Her2-3' UTR" denotes a chimeric mRNA containing the 5' UTR from a luciferase reporter, the luciferase reporter coding sequence, and the 3' UTR of Her2. "Luc" denotes a luciferase mRNA containing the 5' UTR, coding sequence, and 3' UTR from a luciferase reporter construct. MCF-7 cells were transiently transfected with the Luc-Her2-3' UTR or the Luc construct using standard methods, and then analyzed using standard polysome analysis. The lanes of the northern blots are numbered based on the number of ribosomes associated with each mRNA molecule.
Figure 2B:
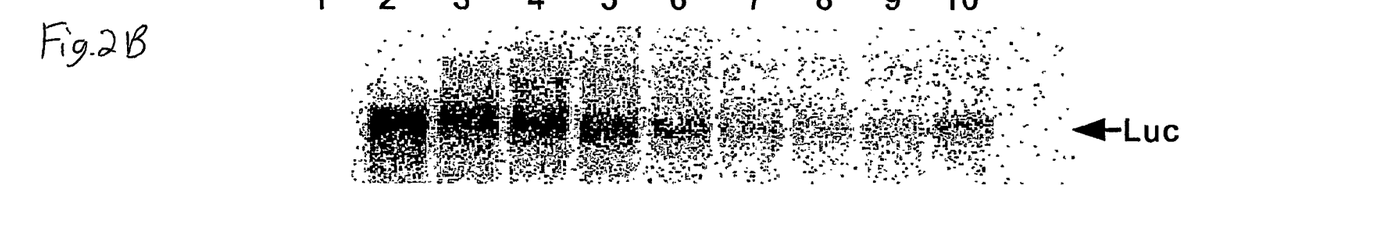

The polysome distribution analysis was performed using standard methods (see, for example, U.S. Provisional Application No. 60/278,902, filed Mar. 26, 2001; Johannes and Sarnow, RNA 4:1500–1513, 1998). Endogenous Her2 mRNA, the chimeric Luc-Her2-3' UTR mRNA, and the luciferase reporter mRNA were predominantly associated with high molecular weight (W) polysomes in stably transfected cells (FIGS. 1A and 1B). In contrast, a smaller percentage of the Luc-Her2-3' UTR mRNA and the luciferase mRNA were associated with HMW polysomes in the transiently transfected cells. This result indicates that the polysome distribution and the resulting translation efficiency of a UTR/reporter mRNA in a stably transfected cell may better mimic the polysome distribution and the translation efficiency of the corresponding endogenous mRNA.

2. Identifying UTRs that Regulate the Function of a UTR/Reporter mRNA

The screen includes an optional first step of identifying host cells in which reporter protein is produced at different levels in the test cells and the control cells. If this step is performed, a 20% difference in reporter protein production is desirable. Methods of quantitating protein levels in cells are described in the literature (Ausubel et al., Current Protocols in Molecular Biology, John Wiley & Sons, 1995). This quantitation step quickly and easily identifies UTR-expressing cells in which the UTR is a potential post-transcriptional regulator. Of course, these differences in expression could also reflect differences at the level of transcription. Therefore, the subsequent step selects for UTR sequences that have post-transcriptional regulatory effects by determining whether the UTR sequences do indeed affect an mRNA functional property of the UTR/reporter transcript, such as mRNA stability, mRNA translational efficiency, the pre-mRNA processing, mRNA localization, mRNA sequestration, or mRNA editing and splicing. Exemplary assays for assessing an mRNA functional property of a transcript are disclosed below. For all of the assays discussed below, a UTR sequence is determined to modulate an mRNA function if the functional value for the control/reporter transcript varies by 20% or more above or below the corresponding value for the UTR/reporter transcript.

A. mRNA Stability

The stability of mRNA can be determined in transfected cells by first blocking transcription with a compound such as actinomycin D (5 μg/ml), and then measuring the degradation rate of the transcripts by quantitating their level in cells harvested at different times. To quantify the level of transcript, total cell RNA purified from harvested cells is subjected to electrophoresis followed by transfer to a filter by pressure blotting. Following incubation, the filter is subject to hybridization by a radiolabeled probe designed to detect the transcript sequence. Additionally, real time PCR with total cell RNA can be used for quantitating mRNA degradation rates. Such degradation rates are calculated, for example, by densitometric scanning of the autoradiographs (Saulnier-Blache et al., Mol. Pharmacol. 50: 1432–42, 1996; Yang et al., J. Biol. Chem. 272: 15466–15473, 1997). A decrease in the rate of degradation indicates an increase in mRNA stability.

B. Transcript Distribution

When transcripts are poorly processed, it may reflect failure of the transcript to move from the nucleus to associate with translationally active ribosomes in the cytoplasm. To assess the effect of the UTR sequences on this function, the cytosolic versus total cellular transcript concentration is compared in UTR/reporter and control/reporter transfected cells. Harvested cells are lysed and subjected to sucrose gradient fractionation. RNA is precipitated from cell fractions, denatured, and blotted onto a nylon membrane in a slot-blot apparatus. Following hybridization to a labeled probe, the transcript RNA levels are quantitated for the various fractions. Alternatively, constructs with or without the UTR sequence can be in vitro labeled with a fluorescent tag and transfected into the cell. Cellular distribution of the transcript is then analyzed using a fluorescent microscope. If the relative quantity of transcript in the cytoplasm compared to total cell transcript RNA is modified when a UTR sequence is present, then this UTR sequence affects cytoplasmic transport of its associated transcripts.

3. Identifying Physiologically Relevant UTR Regulatory Elements

Following the identification of UTR sequences that confer a post-transcriptional regulatory effect on UTR/reporter transcripts as compared to control/reporter transcripts, the next step of the UTR screen identifies UTRs in which this regulatory effect is physiologically relevant. The identification is achieved by comparing one or more functional properties of the host cell's endogenous UTR-associated mRNA transcript to the corresponding property of the UTR/ reporter transcript. (As previously mentioned, the host cells used for the present invention endogenously express the UTR sequence in association with its linked gene.) The mRNA function in the endogenous gene is assessed using the same techniques as described above for the reporter gene transcripts. The UTR-mediated effect on mRNA function in the UTR/reporter transcript is considered physiologically relevant if the value for the mRNA function in the endogenous transcript varies by less than 20% from the UTR/reporter value. In one desirable embodiment, the value for UTR/reporter transcript function does not differ from that of the endogenous transcript by more than 20%. However, if the value of the UTR/reporter transcript function differs from those of the control/reporter transcript and the endogenous transcript, but is closer to that of the endogenous transcript function, it is possible that the UTR contains regulatory elements. The reason the value of the UTR/reporter function does not fully match that of the endogenous transcript function is that additional sequences or folding may be necessary to fully match the value.

If the half-life of a transcript encoding a particular UTR/reporter is greater than the control/reporter transcript, increasing the half life from 1 to 2 hours, the UTR sequence is identified as a candidate sequence having a post-transcriptional regulatory element. The sequence functions by increasing the stability of the transcript. To assess the physiological relevance of this effect, the half life of the transcript encoding the gene endogenously associated with the UTR is measured. If the half-life of the endogenous gene approximates 2 hours, this indicates that the observed effect of the UTR on reporter transcript stability is physiologically relevant and a novel post-transcriptional regulatory element is identified. On the other hand, if the half life of the endogenous transcript is actually 6 hours, then the regulatory effect demonstrated in the UTR/reporter transcript compared to the UTR/control transcript is not physiologically relevant.

Although not required, it is desirable that more than one mRNA functional property be compared between the UTR/reporter transcript and the endogenous UTR-associated transcript to provide a more complete answer regarding the physiological relevance of a post-transcriptional regulatory function. Testing more than one functional property further confirms that the observed UTR regulatory effect on the UTR/reporter transcript is physiologically relevant and is not due to artifactual interactions between the UTR and the reporter sequence.

For example, in the previous example where the regulatory effect of a UTR sequence is found to be physiologically relevant because it increases the half-life of the UTR/reporter transcript from 1 to 2 hours, and the half-life of the endogenous UTR-associated mRNA approximates 2 hours, the physiological relevance of the UTR effect is confirmed if other mRNA functional properties of the endogenous transcript also do not vary by 20% or more above or below the functional value of the UTR/reporter transcript. Thus, if the UTR/reporter mRNA actually demonstrates reduced translational efficiency as compared to the endogenous transcript, the observed UTR regulatory effect on mRNA stability is not considered physiologically relevant.

Further related to identifying physiologically relevant UTR regulatory sequences, it is desirable that the test vectors include both the 5' and 3' UTR sequences of a gene, positioned upstream and downstream, respectively, of the reporter sequence. By using such vectors, the method can detect regulatory effects that result from, or are enhanced by, interactions between the 5' and 3' UTR sequences. If both UTR sequences are not included in the test vector, then the potential is lost for detecting the effects of these interactions on mRNA function. For similar reasons related to mimicking the endogenous function of the UTR, the UTR sequences included in the test vector are preferably the full length sequences.

4. Screening for Compounds That Modulate the UTR Regulatory Elements

After novel UTR sequences are identified as containing physiologically relevant post-transcriptional regulatory sequences, secondary screens for compounds that modulate the effect of these sequences are conducted.

A. In Vivo Screens

In one embodiment of these screens, cell-based assays are used to identify compounds that modulate the in vivo function of the UTR. The cells used in the screen express the UTR sequences endogenously and/or express a transfected UTR/reporter construct. Compounds are administered to the cells and the effect on UTR function is determined by assessing any of the following parameters, either singly or in combination: expression of the endogenous gene; expression of the reporter gene; measuring an mRNA function of the endogenous gene UTR-associated transcript; or measuring an mRNA function of the UTR/reporter transcript. Measures of protein expression and mRNA function are conducted as previously discussed.

When conducting cell-based assays for compound screening, it is desirable that the cells express both a UTR/reporter transcript as well as the endogenous transcript of the gene associated with the UTR. These cells combine the complimentary advantages of ease of detection and physiological relevance. In cells transfected with a UTR/reporter vector, compound-mediated changes in post-transcriptional regulation are easily detected by changes in reporter expression. In cells which endogenously express the UTR-associated gene, the physiological relevance of a compound's modulatory effect can easily be determined by directly measuring the compound's ability to modulate the expression or mRNA function of the endogenous gene.

B. In Vitro Screens

In vitro assays can also be conducted either alone or in combination with the cell-based assays to identify compounds that modulate UTR function. For example, in situations where an identified regulatory UTR sequence interacts with an RNA binding protein (RBP), screening assays are conducted to identify compounds that modulate this interaction. Compounds that alter this interaction may alter mRNA function by altering mRNA stability or translational efficiency.

The methods of detecting such RNA/RBP binding pair interactions are well known in the art, and include, for example, filter binding assays (Wu and Uhlenbeck, Biochemistry 26: 8221–8227, 1987; Carey and Uhlenbeck, Biochemistry 22: 2610–2615, 1983), electrophoretic gel mobility shift assays (Izquierdo and Cuezva, Mol. Cell. Biol. 17:5255–5268, 1997; Malter, Science 246: 664–666, 1989; Zaidi and Malter, J. Biol. Chem. 269: 24007–24013, 1994; Claffey et al., Mol. Biol. Cell 9: 469–481, 1998; Brewer, Mol. Cell. Biol. 11: 2460–2466, 1991); homopolymer beads (Siomi et al., Cell 77: 33–39, 1994), or fluorescence anisotrophy (Tetin et al., Biochemistry 32: 9011–9017, 1993; Goss et al., Nucleic Acids Research 11: 5589–5602, 1983; and Liang et al., WO 98/39484). The screening protocols can be designed to allow simultaneous assessment of the effect of numerous test compounds in a high throughput screening assay, as described in further detail in PCT application WO 98/04923. It is desirable that conditions allowing detection of interactions between nearly every type of RNA and RBP pair be employed. Exemplary protocols, binding conditions, and RNA binding proteins that may be used are disclosed in detail in PCT application WO 98/04923 and are summarized below.

The desirable conditions allow detection of a majority of RNA/RBP interactions. The interactions are facilitated in a binding solution that includes a buffer, a monovalent cation, a divalent cation, a reducing agent, and a density agent. The basic method includes forming a binding solution containing the RNA molecules and binding buffer, heating the solution to denature the RNA, cooling the solution to the reaction temperature to fold the RNA in proper formation, adding RBPs, and detecting the interactions using any suitable procedure. The specificity of binding pair interactions is assessed by comparing the binding in the presence of specific and nonspecific competing RNA. If desired, a competitor of nonspecific RNA/RBP interactions, such as poly r(G), tRNA, heparin, or unrelated RNA molecules of similar length can be added to the binding solution to reduce the background of nonspecific binding. It is desirable that detection involve the separation of interacting RNA molecules and RBPs, such as on the basis of size or physical properties. Two desirable methods are filter binding and gel mobility shift.

Detection of interactions between RNA binding proteins and RNA molecules can be facilitated by attaching a detectable label to the RNA molecule. Generally, labels known to be useful for nucleic acids can be used to label RNA molecules, including, for example, isotopes such as $^{33}P$, $^{32}P$, and $^{35}S$, fluorescent labels such as fluorescein (FITC), 5,6-carboxymethyl fluorescein, sulforhodamine 101 acid chloride (Texas red), nitrobenz-2-oxa-1,3-diazol-4-yl (NBD), coumarin, dansyl chloride, rhodamine, 4'-6-diamini-dino-2-phenylinodole (DAPI), the cyanine dyes (Cy3, Cy3.5, Cy5, Cy5.5, and Cy7), and biotin.

Labeled nucleotides are the desirable form of label since they can be directly incorporated into the RNA molecules during synthesis. Examples of labeled nucleotides include BrdUrd (Hoy and Schimke, Mutation Research 290: 217–230 (1993)), BuUTP (Wansick et al., J. Cell Biology 122:283–293 (1993)) and nucleotides modified with biotin (Langer et al., Proc. Natl. Acad. Sci. USA 78:6633 (1981)) or with suitable haptens such as digoxygenin (Kerhof, Anal. Biochem. 205:359–364 (1992)). Suitable fluorescence-labeled nucleotides are Fluorescein-isothiocyanate-dUTP, Cyanine-3-dUTP and Cyanine-5-dUTP (Yu et al., Nucleic Acids Res. 22:3226–3232 (1994)). A desirable nucleotide analog label for RNA molecules is Biotin-14-cytidine-5'-triphosphate. Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

The RBPs used for screening compounds can be part of a crude or purified cellular or nuclear extract, and can be used either in isolation or in combination. These RBPs can be prepared using known methods of protein extraction and purification (Ashley et al., Science 262: 563–566, 1993; Rouault et al., Proc. Nat. Acad. Sci. USA 86: 5768–5772, 1989; Neupert et al., Nucleic Acids Research 18: 51–55, 1990; Zhang et al., Mol. Cell. Biol. 13: 7652–7665, 1993; and Burd and Dreyfuss, Science 265: 615–21, 1994). Alternatively, known RBPs can be produced recombinantly using standard techniques. DNA encoding RNA binding proteins can be obtained from available clones, by synthesizing a DNA molecule encoding an RNA binding protein with a known amino acid sequence, or by cloning the gene encoding the RNA binding protein. Techniques for recombinant expression and methods for cloning genes encoding known proteins are well known (Sambrook et al., Molecular Cloning, Cold Spring Harbor Laboratory, 1989).

Detection of interactions between RNA binding proteins and RNA molecules can also be facilitated by attaching a detectable label to the RBP. Desirable labels include $^{125}I$, $^{3}H$, $^{35}S$, and, in the case of recombinant proteins, they can be incorporated through the use of labeled amino acids. Techniques for labeling and detecting proteins are known in the art (Sambrook et al. and Ausubel et al., Current Protocols in Molecular Biology, John Wiley & Sons, Inc., 1996). Detection of an RBP can also be achieved by the use of an RBP specific antibody (Johnstone and Thorpe, Immunochemistry in Practice, Blackwell Scientific Publications, 1997).

The screening protocols for identifying compounds that affect RNA/RBP binding pair interactions include, for example, filter binding assays (Wu and Uhlenbeck, Biochemistry 26: 8221–8227, 1987; Carey and Uhlenbeck, Biochemistry 22: 2610–2615, 1983), electrophoretic gel mobility shift assays (Izquierdo and Cuezva, Mol. Cell. Biol. 17:5255–5268, 1997; Malter, Science 246: 664–666, 1989; Zaidi and Malter, J. Biol. Chem. 269: 24007–24013, 1994; Claffey et al., Mol. Biol. Cell 9: 469–481, 1998; Brewer, Mol. Cell. Biol. 11: 2460–2466, 1991); homopolymer beads (Siomi et al., Cell 77: 33–39, 1994), or fluorescence anisotrophy (Tetin et al., Biochemistry 32: 9011–9017, 1993; Goss et al., Nucleic Acids Research 11: 5589–5602, 1983; and Liang et al., WO 98/39484) (see generally, WO 98/04923).

C. Compounds

In general, extracts, compounds, or chemical libraries that can be used in screening assays are known in the art. Examples of such extracts or compounds include, but are not limited to, extracts based on plant, fungal, prokaryotic, or animal sources, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Libraries of genomic DNA or cDNA may be generated by standard techniques (see, e.g., Ausubel et al., supra) and are also commercially available (Clontech Laboratories Inc., Palo Alto, Calif.). Nucleic acid libraries used to screen for compounds that alter gene expression, mRNA function, or RNA/RBP binding pair interactions are not limited to the species from which the RNA or RBP is derived. For example, a Xenopus cDNA may be found to encode a protein that alters a human RNA/RBP interaction.

Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceanographics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods.

When a crude extract is found to modulate an RNA/RBP binding pair interaction or mRNA functionality, further fractionation of the positive lead extract is necessary to isolate the chemical constituents responsible. Thus, the goal of the extraction, fractionation, and purification process is the characterization and identification of a chemical entity within the crude extract having the interaction- or function-modulating activities. The same assays described herein for the detection of interactions in mixtures of compounds can be used to purify the active component and to test derivatives thereof. Methods of fractionation and purification of such heterogenous extracts are known in the art. If desired, compounds shown to be useful agents for treatment are chemically modified according to methods known in the art.

5. Treatment

Compounds which modulate a UTR-mediated effect, such as expression of a UTR-associated gene, or mRNA functionality, or an RNA molecule's RNA/RBP binding pair interaction, may be administered by any appropriate route for treatment or prevention of a disease or condition associated with the expression of the protein endogenously associated with the gene from which the UTR is derived. Examples of such diseases and conditions include neurodegenerative disease, stroke, cardiovascular disease, peripheral vascular disease, high blood pressure, cancer, including breast cancer, inflammatory diseases, such as rheumatoid arthritis, Crohn's disease, diseases associated with cellular proliferation, metabolic disorders, such as obesity and diabetes, and infectious diseases, such as bacterial or viral infections. Administration may be parenteral, intravenous, intraarterial, subcutaneous, intramuscular, intracranial, intraorbital, ophthalmic, intraventricular, intracapsular, intraspinal, intracisternal, intraperitoneal, intranasal, aerosol, by suppositories, or oral administration.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycholate and deoxycholate, or may be oily solutions for administration in the form of nasal drops, or as a gel. The concentration of the compound in the formulation will vary depending upon a number of factors, including the dosage of the drug to be administered, and the route of administration.

The formulations can be administered to human patients in therapeutically effective amounts (e.g., amounts which prevent, eliminate, or reduce a pathological condition) to provide therapy for a disease or condition. Typical dose ranges are from about 0.1 µg/kg to about 1 g/kg of body weight per day. The desirable dosage of drug to be administered is likely to depend on such variables as the type and extent of the disorder, the overall health status of the particular patient, the formulation of the compound excipients, and its route of administration.

6. Regulating Expression of Heterologous Genes

An additional use for the UTR sequences identified as having a post-transcriptional regulatory function is their incorporation into a recombinant construct such that expression of the construct is controlled by the UTR sequence. For example, a nucleic acid sequence identified by the screening method of the invention can be inserted into a heterologous gene to form all or a part of the untranslated region of the gene's mRNA transcript. It is expected that the UTR sequence will function to alter protein expression of the heterologous gene. This is analogous to recombining promoters with heterologous coding regions to alter or control the expression of the coding region.

OTHER EMBODIMENTS

All publications and patent applications mentioned in this specification are herein incorporated by reference.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art. Other embodiments are within the claims.

What is claimed is:

1. A method of identifying one or more candidate compounds having an effect on expression of a gene of interest, said method comprising:
    (a) identifying a 5' or 3' UTR sequence from a gene of interest;
    (b) selecting host cells which express the gene that is endogenously associated with the UTR;
    (c) stably transfecting one set of host cells with a test expression vector, said test vector comprising said 5' or 3' UTR sequence linked to, and positioned upstream or downstream, respectively, of a reporter gene construct (UTR/reporter), and stably transfecting another set of host cells with a control expression vector, said control vector comprising said reporter gene and lacking said UTR sequence (control/reporter);
    (d) identifying whether said UTR sequence has a post-transcriptional regulatory function by assessing whether a first mRNA function of the UTR/reporter transcript is changed compared to the control/reporter transcript;
    (e) determining whether the UTR regulatory function identified in step (d) is physiologically relevant by assessing whether said changed first mRNA function of the UTR/reporter transcript corresponds to the first mRNA function of the gene endogenously associated with the UTR;
    (f) contacting said compound with an mRNA molecule comprising said UTR sequence; and
    (g) measuring whether said compound alters a UTR-mediated effect.

2. The method of claim 1, wherein said compound is contacted with a cell that expresses said mRNA molecule.

3. The method of claim 1, wherein said UTR-mediated effect is a change in mRNA function.

4. The method of claim 1, wherein said compound is contacted with said mRNA molecule in vitro, and further wherein said UTR-mediated effect is an interaction between an mRNA transcript comprising said UTR and an RNA binding protein.

5. The method of claim 2, wherein the UTR-mediated effect is the expression of a gene linked to said UTR sequence.

* * * * *

UNITED STATES PATENT AND TRADEMARK OFFICE
CERTIFICATE OF CORRECTION

PATENT NO. : 7,078,171 B2  Page 1 of 1
APPLICATION NO. : 10/258930
DATED : July 18, 2006
INVENTOR(S) : Giordano et al.

It is certified that error appears in the above-identified patent and that said Letters Patent is hereby corrected as shown below:

Column 4,
 Line 11, replace "anisotrophy" with --anisotropy--;
 Line 22, replace "northern" with --Northern--;
 Line 36, replace "northern" with --Northern--; and
 Line 53, replace "northern" with --Northern--.

Column 10, Line 62, replace "anisotrophy" with --anisotropy--.

Column 12, Line 29, replace "anisotrophy" with --anisotropy--.

Column 13,
 Line 39, replace "napthalenes" with --naphthalenes--; and
 Line 48, replace "glycholate" with --glycolate--.

Column 14, Line 64, replace "effect is" with --effect that is measured is--.

Signed and Sealed this

Twenty-eighth Day of November, 2006

JON W. DUDAS
*Director of the United States Patent and Trademark Office*